(12) United States Patent
Bhattacharyya et al.

(10) Patent No.: US 7,144,921 B2
(45) Date of Patent: Dec. 5, 2006

(54) COMPOSITION HAVING ANTIBACTERIAL AND ANTIFUNGAL PROPERTIES

(75) Inventors: Asok Kumar Bhattacharyya, Calcutta (IN); Alok Pal, Calcutta (IN); Samir Bhattacharya, Calcutta (IN)

(73) Assignee: Council of Scientific and Industrial Research, New Dehli (IN)

( * ) Notice: Subject to any disclaimer, the term of this patent is extended or adjusted under 35 U.S.C. 154(b) by 277 days.

(21) Appl. No.: 10/233,427

(22) Filed: Sep. 4, 2002

(65) Prior Publication Data
US 2003/0134004 A1  Jul. 17, 2003

Related U.S. Application Data

(60) Provisional application No. 60/316,263, filed on Sep. 4, 2001.

(51) Int. Cl.
*A01N 31/00* (2006.01)
(52) U.S. Cl. ............... 514/739; 514/841; 514/842
(58) Field of Classification Search ........... 514/733, 514/725, 841, 842, 739; 424/195.1, 430, 424/433
See application file for complete search history.

(56) References Cited

U.S. PATENT DOCUMENTS 4,384,003 A * 5/1983 Kazmiroski et al. ........ 424/341

OTHER PUBLICATIONS

Sharma et al, 73CA:63961, 1970.*
Wagner et al, 138CA;36374, 2002.*
Fukuda et al, 105CA:38690, 1986.*
Rotmistrov et al, 51CA:58035, 1957.*
Remington's Pharmecutical Sciences 17th ED., Gennaro et al Eds, Phila Coll. Pharm. Phila PA, 1985, p. 1158.*
Buch et al., Indian Journal of Medical Research, 1988;87:361-363.*

* cited by examiner

*Primary Examiner*—San-Ming Hui
(74) *Attorney, Agent, or Firm*—Birch, Stewart, Kolasch & Birch, LLP

(57) ABSTRACT

The present invention provides for the use of oil of clove which causes instant immobilization of human spermatozoa both in presence of seminal fluid as well as in presence of female reproductive tract fluids, including uterine components and cervical mucus and also be useful for treating and/or preventing the common vaginal infections.

14 Claims, 1 Drawing Sheet

Clove oil
Dilution
A: $10^{-7}$
B: $10^{-5}$
C: $10^{-3}$

Effect of varied clove oil dilutions on motility of human, hamster and rat sperm.

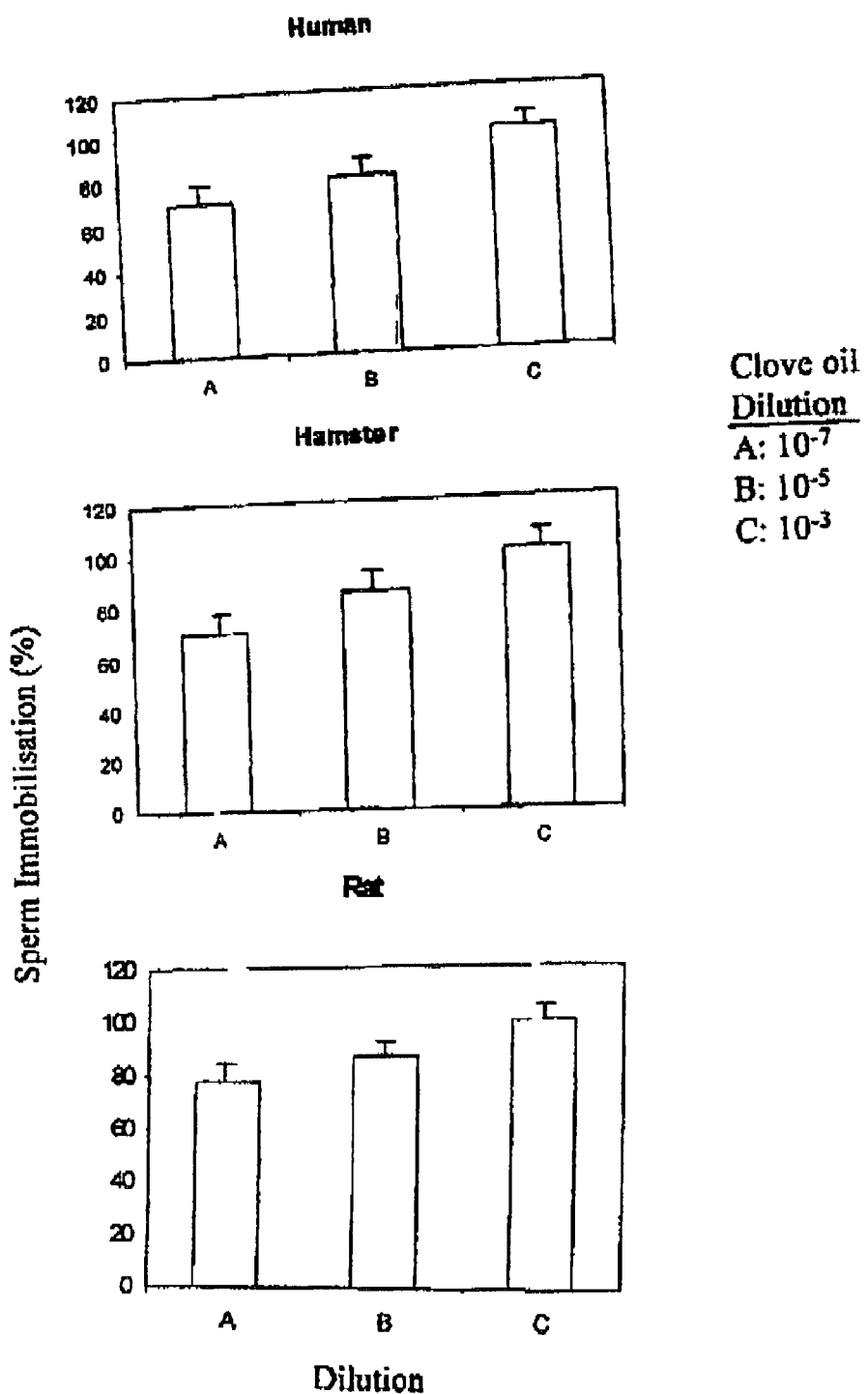
Fig. 1 Effect of varied clove oil dilutions on motility of human, hamster and rat sperm.

COMPOSITION HAVING ANTIBACTERIAL AND ANTIFUNGAL PROPERTIES

The present application claims priority from the U.S. Provisional application Ser. No. 60/316,263 filed on Sep. 4, 2001.

FIELD OF THE INVENTION

The present invention relates to the use of oil of clove which causes instant immobilization of human spermatozoa both in presence of seminal fluid as well as in presence of female reproductive tract fluids, including uterine components and cervical mucus. The invention may also be useful for treating and/or preventing the common vaginal infections.

BACKGROUND AND PRIOR ART REFERENCES

Conservatives estimates predict a nearly 50% increase in the current world population of approximately six billion people by the year 2050 (1998 United Nations. 1998 *Revision of the official United Nations population estimates and projections*. World population nearing 6 billion projected close to 9 billion by 2050, Population Division of the Department of Economics and Social Affairs. United Nations, New York, 998). This potential over-population, particularly in developing countries, is further complicated by the non-availability of proper easy-to-use, simple, cheap, least toxic and non-invasive method of contraception. Several contraceptive devices have been introduced till date and all of them suffer from certain constraints as enumerated below:

Though hormonal methods (oral contraceptives) are highly effective in preventing pregnancies, various complications and side effects on prolonged use can not be ruled out.

On the other hand, vasectomy and ligation of Fallopian tube never became popular because of their various complications, irreversibility and problems of recannulation.

The intrauterine devices (IUDs) also cause several complications, including uterine perforations, occasional bleeding etc.

The vaginal preparations are however relatively popular all over the world amongst the motivated couples, and because of their local and non-systemic application. However, these never give 100% contraceptive assurance.

The vaginal contraceptive compositions marketed in the USA primarily utilize nonionic detergents (surfactants) as their active ingredient. Of these, the most commonly used is nonoxynol-9 (N-9). Although N-9 is an extremely potent sperm immobilizing agent in vitro, but the marketed preparations are encountered with failures due to several reasons including the possibility of escape of first fraction of ejaculated sperms from its interaction with the active agents. In addition, N-9 can interfere with the natural vaginal environment and can cause irritation at a concentration that is recommended for use. N-9 and other spermicidal agents that have surfactant and cytotoxic properties have been proposed to prevent conception as a dispersing agent in spermicidal preparations (namely, Delfen, Gentersal and Ortho-Crème). However, relatively high failure rate of these surfactants in preventing pregnancies as well as evidence of adverse side effects have been documented (Stafford et al., 1998 Stafford, M K, Ward, H. Flanagan, A, Rosenstein, I J, Taylor-Robinson, D, Smith, J R, Weber, J and Kitchen, VS. Safety study of nonoxynol-9 as a vaginal microbicide: evidence of adverse effects. Journal of Acquired Immune Deficiency Syndromes, 17:327–331, 1998., Roddy et al., 1998—Roddy, R E, Zekeng, L, Ryan, K A, Tamoufe, U, Weir, S S and Wong, E L. A controlled trial of nonoxynol-9 film to reduce male-to-female transmission of sexually transmitted diseases—New England Journal of Medicine, 339: 504–510, 1998 and Homn. R E, Foldesy, R G and Hahn, D W. ORF 13904, a new long-acting vaginal contraceptive. Contraception, 32: 267–274, 1985).

For the last few decades, clove oil is being used in dental cream, mouthwash and various medicinal preparations at concentrations much higher than that cause sperm immobilization For these reasons, it is imperative that a new type of highly active ingredient be identified and developed for vaginal contraceptive use, as it will be noninvasive and is expected to have least or no side effects.

OBJECTS OF THE INVENTION

The main object of the present invention is to provide a highly specific, safe and stable contraceptive composition for women to protect themselves from unexpected pregnancies and vaginal infections.

Another object of the invention is to provide an antifertility composition comprising clove oil with a dilunet and optionally with one or more pharmaceutically acceptable additives.

Still another object of the invention is to provide a composition for spontaneous immobilization of sperms of human, hamster and rats.

Yet, another object of the invention is to provide a composition, which causes irreversible inhibition of hyaluronidase and acrosin, the essential enzymes for fertilization.

Yet another object of the invention, is to provide a composition causes irreversible damage to the sperm cells with complete loss of motility even in presence of seminal fluid of men, uterine washings and cervical mucus of women.

Still another object of the invention is to provide an innovative noninvasive contraceptive, which results in instantaneous immobilization with such a low dose $10^{-3}$ to $10^{-4}$ of active component.

Still another object of the invention is to provide a method of immobilizing mammalian spermatozoa.

SUMMARY OF THE INVENTION

Accordingly, the present invention relates to the use of oil of clove which causes instant immobilization of human spermatozoa both in presence of seminal fluid as well as in presence of female reproductive tract fluids, including uterine components and cervical mucus.

The present invention also relates a contraceptive composition, that can be used vaginally by women to protect themselves from unexpected pregnancies and vaginal infections; a highly specific, safe, stable, and comparatively cheap active ingredient has been discovered.

The efficacy has been further proven by hamster and rat spermatozoa, which were immobilized instantaneously with very low concentration of (1:1000) oil. The present invention comprises in vitro as well as in vivo methods for complete prevention of human sperm motility, thereby making sperm entry impossible into upper genital tract (i.e.

uterus, Fallopian tube etc.) of women. The invention may also be useful for treating and/or preventing the common vaginal infections.

DETAILED DESCRIPTION OF THE INVENTION

Accordingly, the present invention provides a composition useful as an anti fertility agent and anti microbial agent in mammals including human beings, said composition comprising effective amount of clove oil, diluent and optionally one or more pharmaceutically acceptable additives.

In accordance to the objectives, the present invention provides Anti-fertility or a contraceptive composition comprising:
i) clove oil as an active component;
ii) aqueous alcohol;
iii) BWW medium as an diluent; and
iv) optionally one or more pharmaceutically acceptable additive.

In an embodiment, the aqueous alcohol used contains 30% alcohol

Another embodiment, the said composition comprising clove oil: 30% aq.alcohol:BWW medium in the ratio of 0.5:0.5:1000 to 0.5:0.5:10000000, and preferably consists of clove oil: 30% aq.alcohol:BWW medium in the ratio ranging between 0.5:0.5:1000 and 0.5:0.5:50,000.

Still another embodiment, the pharmaceutically acceptable ingredients used is selected from talc, magnesium stearate, cellulose, calcium carbonate, starch-gelatin paste and/or carriers, excipients, diluents or solvents.

Still another embodiment, BWW medium consists of 94 mM NaCl, 4.7 mm KCl, 1.7 mM $CaCl_2$, 1.2 mM $KH_2PO_4$, 1.2 mM $MgSO_4 \cdot 7H_2O$, 25 mM $NaHCO_{3.0.5}$ mM Sodium pyruvate, 19 mM Sodium acetate, 5 mM glucose, 0.4% BSA, 0.1% penicillin/streptomycin, said medium having a pH 7.2.

Yet another embodiment, the said composition immobilize human spermatozoa spontaneously within 10 seconds by a 1:1 aqueous alcoholic clove oil solution diluted 1,000 times with BWW medium.

In still another embodiment, the said composition provides complete inhibition of motility in about a minute by 1:1 aqueous alcoholic clove oil solution diluted 10,000 times with BWW medium.

Yet another embodiment, the composition provides for an innovative noninvasive contraceptive, which results in instantaneous immobilization having the active component concentration, is in the range of $10^{-3}$ to $10^{-4}$.

Yet another embodiment, the composition causes irreversible inhibition of hyaluronidase and acrosin, the essential enzymes for fertilization Yet another embodiment, the composition totally disrupts the plasma membrane of sperms and destroys the sperm acrosomal enzyme.

Yet another embodiment, hyaluronidase (EC 3.2.1.35), and acrosin (EC 3 2.21.10) are greatly inhibited to the extent of 90 %, by a 1:1 aqueous alcoholic clove oil solution diluted 1,000 times with BWW medium, resulting in irreversible inhibition of enzymes.

Still another embodiment, 5'-nucleotidase, that is associated with the sperm plasma membrane, is totally dispersed and dissociated in the medium at 1,000 times dilution of oil indicating the destabilization of the sperm membrane system.

Yet another embodiment, the composition causes irreversible damage to the sperm cells with complete loss of motility even in the presence of seminal fluid, uterine washings and cervical mucus.

Still another embodiment, the said composition may be used as capsule, sponge, cream, vaginal film and any other preparations that can be controlled by self administration.

Yet another embodiment, the said composition immobilizes sperms from humans, hamster and rats.

Still another embodiment, the said composition further provides anti-microbial characteristics against vaginal infections.

Yet another embodiment, the said composition inhibits the microbial growth of fungi selected from a group consisting of cocci, *candida* and *trichomonas*.

Yet another embodiment, wherein the composition inhibits the microbial growth of fungi by 1:1 aqueous alcoholic clove oil solution diluted 100 times with BWW medium.

Still another embodiment, the composition may be administered by in-vitro as well as in vivo methods for complete prevention of human sperm motility.

One more embodiment of the invention provides a method of immobilizing mammalian spermatozoa said method comprising treating/contacting the spermatozoa with a composition comprising:
i) clove oil as an active component;
ii) aqueous alcohol;
iii) BWW medium as an diluent; and
iv) optionally one or more pharmaceutically acceptable additive Another embodiment, 5'-nucleotidase, that is associated with the sperm plasma membrane, is totally dispersed and dissociated in the medium at 1,000 times dilution of oil indicating the destabilization of the sperm membrane system, which is essential for the maintenance of motility.

In an embodiment of the invention, the clove oil and its ingredients have been found highly effective in immobilizing human spermatozoa. Spontaneous immobilization occurs within 10 seconds at more than 1,000 times dilution of the oil. Complete inhibition of motility has been observed in about a minute even at 10,000 dilution in all types of sperm samples obtained from proven fertile men (vide Tables 1 and 2).

Yet another embodiment of the invention provides for an innovative noninvasive contraceptive which results in instantaneous immobilization with such a low dose $10^{-3}$ to $10^{-4}$ of active component.

Further, yet another embodiment of the invention reveals the damage and perforation of plasma membrane system, which surrounds the mammalian sperm cells, that causes the total immobilization with occasional agglutination of human sperms, along with loss membrane components that are necessary for the fertilization to occur.

Yet another embodiment of the invention relates to the use of the composition for total immobilization with occasional agglutination of human sperms, along with loss membrane components that arm necessary for the fertilization occurs.

Yet another embodiment of the invention relates to irreversible inhibition of hyaluronidase and acrosin, the essential enzymes for fertilization.

Yet another embodiments of the invention provide total disruption of the plasma membrane of human sperms and destroy the sperm acrosomal enzyme.

Yet another embodiment relates to the irreversible damage to the sperm cells with complete loss of motility even in presence of seminal fluid of men, and uterine washings and cervical mucus of women.

Yet another embodiment of the invention relates to anti bacterial activity of the clove oil dilution. The clove oil inhibits the microbial growth of fungi including cocci, *candida* and *trichomonas*.

Yet another embodiment invention relates to anti-bacterial and anti fungal activities of clove oil, that inhibits the microbial growth of fungi including cocci, *candida* and *trichomonas* at 100 times dilution (Table 5).

Yet another embodiment of the invention relates to activity of clove oil active principles, that are also effective in immobilizing rat and hamster spermatozoa collected from epididymis.

Yet another embodiment of the invention relates to wherein, sperms are totally immobilized almost instantaneously with more than 1000 times dilution of clove oil, By showing total inhibitory activity towards human sperms even with low concentration of clove oil.

Yet another embodiment of the invention, the ratio of clove oil to the diluent is in the range between 1:1000 to 1;50,000.

Yet another embodiment of the invention, the composition may be administered by in-vitro as well as in vivo methods for complete prevention of human sperm motility, thereby making sperm entry impossible into upper genital tract namely uterus, Fallopian tube etc. of women.

Yet another embodiment of the invention, the said composition may be used as capsule, sponge, cream, vaginal film and any other preparations that can be controlled by self administration.

Another embodiment relates to the synergic activity of antifertility and anti microbial is due to common mechanism of action that exists for prevention of fertilization by sperm immobilization and inhibition of vaginal infection.

Another embodiment of the present invention relates to potential contraceptive agent that acts as an inhibitor of hyaluronidase and acrosin enzymes, essential for fertilization.

In another embodiment hyaluronidase (EC 3.2.1.35), and acrosin (EC 3.2.21.10) are greatly inhibited to the extent of 90 %, at a very low concentration, which is achieved on incubation of the sperm cells with 1,000 times diluted clove oil, resulting in irreversible inhibition of enzymes.

Another embodiment of the invention relates to 5'-nucleotidase, that is associated with the sperm plasma membrane, is totally dispersed and dissociated in the medium at 1.000 times dilution of oil indicating the destabilization of the sperm membrane system—the organization and the intactness of which is essential for the maintenance of motility.

Another embodiment relates to clove oil acting as highly potent agents to disrupt the plasma membrane of human sperms and destroys the sperm acrosomal enzyme, which is an irreversible damage to the sperm cells with complete loss of motility even in presence of seminal fluid of men, and uterine washings and cervical mucus of women.

Another embodiment of the invention, consistent with its action on human sperm, clove oil active principles are also effective in immobilizing rat and hamster spermatozoa collected from epididymis. All sperms are totally immobilized almost instantaneously with more than 1000 times dilution of clove oil.

Another embodiment relates to the composition showing total inhibitory activity towards human sperms, at a very low concentration to exhibit the desired effect when inserted as capsule or otherwise in the vagina prior to copulation.

BRIEF DESCRIPTION OF THE ACCOMPANYING DRAWINGS

FIG. 1 shows the results of this experiment where different dilution of clove oil was examined on human, hamster and rat sperm motility. Clove oil addition in different dilution immobilized the sperm in a dose dependent manner. $10^{-3}$ dilution effected 100% immobilization of human, hamster and rat sperm in 15 sec. There was practically very little difference between the doses and the source of sperm sample.

The invention is further described in the form of the following examples which shall not be construed as a limit to the scope of the invention.

EXAMPLES

Example 1

Sperm Immobilizing Assays

Inhibition and immobilization of human sperm motility were evaluated by mixing 100 μL of test solution with 100 μL of freshly ejaculated semen. Immediately after mixing (within 10 seconds), the percentage of motile spermatozoa was determined by microscopic examination (400× and 100×). At higher dilution incubation time was 60 seconds. The dose-response data have been presented in Table 3.

Example 2

Other Techniques:

Hyaluronidase (EC 3.2.1.35) activity was quantified with hyaluronic acid as a substrate. This was measured by determining the concentration of N-acetylglucosamine reactive material, resulting from enzyme action Table 4(*a*).

Human acrosin (EC 3.4.21.10) activity was measured by following the kinetics of change in optical density at 253 nm; the hydrolysis of N∝-benzoyl-L-arginine ethyl ester (BAEE) was quantified Table 4(*b*).

Nucleotidases were assayed by using 5'-AMP and β-glycerophosphate as substrate, and the enzyme activities are expressed in terms of free phosphates that are released Table 4(*c*).

Example 3

Caudal spermatozoa from rats and hamsters and ejaculated sperm from six normospermic human donor (aged between 30–37) were used to observe clove oil effect in the motility of sperm. Clove oil was diluted to 1000 times and added to the sperm sample. Human sperm after collection were allowed to liquefy at 37° C. for 30 minutes. The liquefied samples were diluted with equal volume of Ham's F-10 medium and centrifuged at 5000 g for 10 minutes. Sperm pellets were then layered with 1.0 ml of Ham's F-10 medium and were incubated at 37° C. which permitted the progressive swimming up of the motile cells and counted in a Makler's chamber. Only the cells with high motility were used in the experiments. Hamster and rat sperm were diluted in HWW medium (94 mM NaCl, 4.7 mM KCl, 1.7 mM $CaCl_2$, 1.2 mM $KH_2PO_4$, 1.2 mM $MgSO_4$, $7H_2O$, 25 mM $NaHCO_3$, 0.5 mM sodium pyruvate, 19 mM sodium acetate, 5 mM glucose, 0.4% BSA, 0.1% penicillin/streptomycin, pH 7.2), pre equilibrated in a $CO_2$ incubator for 30 minutes to swim them up and only highly motile sperm were selected and centrifuged at 1000 g for 2 minutes. The pellet containing highly motile sperm were diluted in BWW medium and counted in a Makler's chamber. In all the cases, i.e. human, hamster and rat, 25–35 million sperm were taken for clove oil experiment.

Whether this immobilization was due to the death of the sperm by clove oil or not was tested by using cosin-nigrosin vital dye uptake and this clearly showed mortality of the sperm. The same concentration of clove oil did not show any adverse effect on vaginal epithelial cells; therefore appears to be safe for its probable use as vaginal contraceptive.

How clove oil at a dilution of $10^{-3}$ can completely immobilize, human, hamster and rat sperm by causing death to them is not yet clear. Since there is a possibility to immobilize through the destabilization of sperm membrane architecture, we selected two sperm membrane bound enzyme, acrosin and 5'-nucleotidase as markers to study this aspect. The outer envelope of most of the mammalian spermatozoa is rich in polar phospholipid and any alteration to this phospholipid affects sperm motility or survival. Acrosome matrix is a part of this complex where acrosin remains in the bound form. Any disturbance in membrane architecture induces acrosome reaction, which in turn results acrosin release. Similarly, 5'-nucleotidase is an enzyme bound to the membrane of sperm. This enzyme anchors glycophosphatidylinositol network in the sperm membrane and therefore when it gets free from its anchorage, an alteration in membrane structure is expected. Tables 6 and 7 demonstrate the result of clove oil addition (at a dilution of $10^{-3}$) to the sperm of six human donors. Both acrosin and 5'-nucleotidase activities could be located in the supernatant fraction on clove oil treatment. In the control sperm, both the marker enzyme activities was obtained in the sperm pellet where supernatant showed very little activity. On treating the human sperm with clove oil, the marker enzyme activities were found to be located in the supernatant which clearly shows the detachment of the enzymes from the membrane architecture. These results strongly suggest clove oil target to be the sperm membrane and by acting through the membrane, it destabilizes the sperm structure causing immobilization and death. All these are novel findings with clove oil that supports its use as an effective contraceptive.

Composition of BWW medium: 94 mM NaCl, 4.7 mM KCl, 1.7 mM $CaCl_2$, 1.2 mM $KH_2PO_4$, 1.2 mM $MgSO_4$, $7H_2O$, 25 mM $NaHCO_3$, 0.5 mM sodium pyruvate, 19 mM sodium acetate, 5 mM glucose, 0.4% BSA, and 0.1% antibiotic (penicillin/streptomycin) solution

TABLE 1

EFFECTS OF CLOVE OIL ON HUMAN SPERM IMMOBILIZATION

| Dilution Factor | Percent Motility | Dilution Factor | Percent Motility |
|---|---|---|---|
| 0 | 0 | 0 | 0 |
| 10 | 0 | 10 | 0 |
| 100 | 0 | 100 | 0 |
| 1,000 | 0 | 1,000 | 0 |
| 10,000 | 0 | 10,000 | 0 |
| 50,000 | 0 | 50,000 | 0 |
| 100,000 | 1.1 | 100,000 | 0.1 |
| 500,000 | 2.4 | 500,000 | 1.3 |
| 1,000,000 | 3.3 | 1,000,000 | 2.3 |
| 10,000,000 | 5.6 | 10,000,000 | 4.6 |
| 100,000,000 | 9.1 | 100,000,000 | 6.5 |

Normospermic, Count 56 million/ml
Normospermic, Count 40 million/ml

TABLE 2

| Dilution Factor | Percent Motility | Dilution Factor | Percent Motility |
|---|---|---|---|
| 0 | 0 | 0 | 0 |
| 10 | 0 | 10 | 0 |
| 100 | 0 | 100 | 0 |
| 1,000 | 0 | 1,000 | 0 |
| 10,000 | 0 | 10,000 | 0 |
| 50,000 | 0 | 50,000 | 0.1 |
| 100,000 | 0 | 100,000 | 0.7 |
| 500,000 | 2.1 | 500,000 | 4.3 |
| 1,000,000 | 2.3 | 1,000,000 | 7.3 |
| 10,000,000 | 4.6 | 10,000,000 | 11.1 |
| 100,000,000 | 10.5 | 100,000,000 | 23.3 |

Oligoospermic, Count 19 million/ml
Hyperspermic, Count 120 million/ml

All categories of sperm cells were incubated for 60 seconds, and checked under microscope at 100× and 400×.

TABLE 3

IMMOBILIZATION OF RAT AND HAMSTER EPIDIDYMAL SPERMS

| Dilution Factor | Percent Motility (Rat Sperm) | Dilution Factor | Percent Motility (Hamster Sperm) |
|---|---|---|---|
| 0 | 0 | 0 | 0 |
| 10 | 0 | 10 | 0 |
| 50 | 0 | 50 | 0 |
| 100 | 0 | 100 | 0 |
| 500 | 0 | 500 | 0 |
| 1,000 | 10* | 1,000 | 50* |
| 2,000 | 10** | 2,000 | 50** |

*Incubation time was 10 seconds:
**Incubation time was 60 seconds

Inhibition of Human Sperm by Hyaluronidase and Acrosin by Clove Oil

TABLE 4(a)

| | Acrosin activity (mIU/million sperm) |
|---|---|
| Control Expt. | 6.75 |
| Experimental (with 1000 times diluted clove oil) | 0.76 |

TABLE 4(b)

| | Hyaluronidase activity (units) |
|---|---|
| Control Expt. | 63.8 |
| Experimental (with 1000 times diluted clove oil) | 6.9 |

Inhibition of Human Sperm 5'-nucleotidase by Clove Oil

TABLE 4(c)

| Control Expt. | 9.5 |
|---|---|
| Experimental (with 1000 times diluted clove oil) | 0 |

Inhibition of Cocci, Candida and Trichomonas by Clove Oil

TABLE 5

| | Percent inhibition by cup method (using 100 times diluted clove oil) |
|---|---|
| S. cocci | 60 |
| Candida albicans | 45 |
| Trichomonas | 33 |

TABLE 6

ACROSIN RELEASE FROM HUMAN SPERM ACROSOME BY CLOVE OIL

| | | | Acrosin activity (mIU/min/3 × $10^7$ sperms) | | | |
|---|---|---|---|---|---|---|
| | Total | Progres- | Control | | Clove oil treated | |
| Human Donor No. | Sperm count (×$10^6$) | sively motile cells (×$10^6$) | Sperm Pellet | Super-natant | Sperm pellet | Super-natant |
| 1. | 40.0 | 36.1 | 150.0 | 31.0 | 7.5 | 100.7 |
| 2. | 43.8 | 32.0 | 180.6 | 29.6 | 4.6 | 92.6 |
| 3. | 63.0 | 50.0 | 160.3 | 27.0 | 5.0 | 88.4 |
| 4. | 68.5 | 35.0 | 63.6 | 33.0 | 6.9 | 124.0 |
| 5. | 89.0 | 55.2 | 122.5 | 24.6 | 2.1 | 109.0 |
| 6. | 91.5 | 72.0 | 145.1 | 36.5 | 8.5 | 122.7 |

TABLE 7

5'-NUCLEOTIDASE DETACHMENT FROM HUMAN SPERM BY CLOVE OIL

| | | | 5'-nucleotidase activity (μg phosphate released/h/3 × $10^7$ sperms) | | | |
|---|---|---|---|---|---|---|
| | Total | Progres- | Control | | Clove oil treated | |
| Human Donor No. | Sperm count (×$10^6$) | sively motile cells (×$10^6$) | Sperm Pellet | Super-natant | Sperm pellet | Super-natant |
| 1. | 40.0 | 35.1 | 32.9 | 10.5 | 7.9 | 89.6 |
| 2. | 63.0 | 45.0 | 48.0 | 15.5 | 8.2 | 98.2 |
| 3. | 63.5 | 50.6 | 54.9 | 19.0 | 2.0 | 85.0 |
| 4. | 88.0 | 57.5 | 37.0 | 11.9 | 9.3 | 106.6 |
| 5. | 91.5 | 65.0 | 47.5 | 16.9 | 8.8 | 99.5 |
| 6. | 103.0 | 75.1 | 55.0 | 16.6 | 7.5 | 69.8 |

The invention claimed is:

1. A method of immobilizing mammalian spermatozoa, said method comprising treating/contacting the spermatozoa with a composition comprising ethanol and clove oil, in a ratio of about 1:3 diluted with a pharmaceutically acceptable diluent in a range of from 1:2000 to 1:20,000,000.

2. The method as claimed in claim 1, wherein spermatozoa are selected from humans, hamster and rats.

3. The method as claimed in claim 1, wherein the pharmaceutically acceptable diluent is BWW medium.

4. The method as claimed in claim 1, wherein immobilization of human spermatozoa occurs within 10 seconds.

5. The method as claimed in claim 1, wherein the said composition provides complete inhibition of motility in about one minute.

6. The method as claimed in claim 1, wherein the composition is diluted in the range of 1:2000 to 1:20,000, the composition is applied to the vaginal cavity and provides immobilization of sperm within 10 seconds of contact of sperm with the composition.

7. The method as claimed in claim 1, wherein the composition causes irreversible inhibition of hyaluronidase and acrosin.

8. The method as claimed in claim 1, wherein the composition totally disrupts the plasma membrane of human sperms and destroys the spermacrosin.

9. The method as claimed in claim 1, wherein the dilution of the aqueous alcohol and clove oil is sufficient to cause dissociation of 5'-nucleotidase that is associated with the sperm plasma membrane.

10. The method as claimed in claim 1, wherein the composition causes irreversible damage to the sperm cells with complete loss of motility even in presence of seminal fluid, uterine washings and cervical mucus.

11. The method as claimed in claim 1, wherein the composition is in at least one preparatory form selected from the group consisting of capsule, sponge, cream, and vaginal film.

12. The method as claimed in claim 1, wherein the composition formulated in a capsule and the capsule is inserted in the vagina prior to copulation.

13. The method as claimed in claim 1, wherein the composition further comprises at least one pharmaceutically acceptable additive selected from the group consisting of talc, magnesium stearate, cellulose, calcium carbonate and starch-gelatin paste.

14. The method as claimed in claim 1, wherein the composition is in a preparatory form that can betopically administered to the vaginal cavity.

* * * * *